United States Patent [19]
Kelly et al.

[11] Patent Number: 5,380,196
[45] Date of Patent: Jan. 10, 1995

[54] ORTHODONTIC BRACKET WITH ARCHWIRE SLOT LINER

[75] Inventors: John S. Kelly, Arcadia; James D. Hansen, Duarte; Joseph M. Caruso, Aguadulce, all of Calif.

[73] Assignee: Minnesota Mining and Manufacturing Company, St. Paul, Minn.

[21] Appl. No.: 61,164

[22] Filed: May 13, 1993

[51] Int. Cl.⁶ ............................................. A61C 3/00
[52] U.S. Cl. ............................................. 433/8; 433/10
[58] Field of Search ............... 433/8, 9, 10, 11, 12, 433/13, 14, 16, 17, 22

[56] References Cited

U.S. PATENT DOCUMENTS

| | | | |
|---|---|---|---|
| 2,908,974 | 10/1959 | Stifter | 32/14 |
| 3,469,314 | 9/1969 | Pearlman | 32/14 |
| 3,504,438 | 4/1970 | Wittman et al. | 32/14 |
| 3,775,850 | 12/1973 | Northcutt | 32/14 A |
| 3,930,311 | 1/1976 | Andrews | 32/14 A |
| 3,964,165 | 6/1976 | Stahl | 32/14 A |
| 4,186,488 | 2/1980 | Wallshein | 433/8 |
| 4,249,897 | 2/1981 | Anderson | 433/8 |
| 4,299,569 | 11/1981 | Frantz | 433/8 |
| 4,302,532 | 11/1981 | Wallshein | 433/8 |
| 4,531,911 | 7/1985 | Creekmore | 433/8 |
| 4,639,218 | 1/1987 | Jones et al. | 433/8 |
| 4,674,978 | 6/1987 | Acevedo | 433/8 |
| 4,850,865 | 7/1989 | Napolitano | 433/8 |
| 4,954,080 | 9/1990 | Kelly et al. | 433/8 |
| 5,203,804 | 4/1993 | Nikutowski et al. | 433/8 |
| 5,252,066 | 10/1993 | Fairhurst | 433/8 |
| 5,254,002 | 10/1993 | Reher et al. | 433/8 |

*Primary Examiner*—Cary E. O'Connor
*Assistant Examiner*—Nicholas D. Lucchesi
*Attorney, Agent, or Firm*—Gary L. Griswold; Walter N. Kirn; James D. Christoff

[57] ABSTRACT

An orthodontic bracket, such as a bracket made of ceramic material, is provided with a liner that enhances sliding mechanics between the bracket and an archwire. A portion of the liner projects beyond the bracket body and optionally includes an occlusal, gingival or lingual section that extends over a mesial or distal side of the bracket body. A bottom surface of the liner is located a distance from a bottom wall of a channel receiving the liner, and the distance optionally varies along the length of the archwire slot in order to urge the attached tooth to rotate as needed about its long axis. The liner is bonded to the bracket body in such a manner that the bracket body is thereafter held by the liner in compression.

23 Claims, 4 Drawing Sheets

ORTHODONTIC BRACKET WITH ARCHWIRE SLOT LINER

BACKGROUND OF THE INVENTION

1. Field of the Invention

This invention relates to a bracket that is used in orthodontic therapy and has an archwire slot liner for enhancing sliding movement of the bracket along an archwire coupled to the bracket.

2. Description of the Related Art

In orthodontic treatment, tiny devices known as brackets are secured to the patient's teeth. An archwire is received in a slot of each bracket, and is held in place in the slots by ligating wires or by small elastic 0-rings that extend around each bracket and the archwire. The teeth connected to the brackets are urged toward orthodontically correct positions by bends or twists placed in the archwire, or by elastomeric modules interconnecting certain brackets. The archwire serves as a track to guide sliding movement of the brackets so that the associated teeth are shifted toward desired positions.

In the past, orthodontic brackets were often made of stainless steel, and archwires were made of stainless steel or alloys containing stainless steel, nickel and titanium. In general, frictional resistance to sliding movement of the metal brackets, while not insignificant, is a factor that is not considered unsatisfactory by most orthodontists. However, metal brackets are not aesthetic and are sometimes referred to as a "tin grin" that may be an embarrassment to the patient.

Orthodontic brackets made of non-opaque plastic materials such as polycarbonate have been introduced by various manufacturers over the years. Unfortunately, some plastic brackets exhibit undue deformation of the archwire slots because of creep of the material as orthodontic forces are applied by the wire to the brackets. Undue deformation of the archwire slots may prevent precise control of movement of the associated teeth, and in some instances may cause the brackets to fracture. Replacement of brackets during orthodontic treatment is time consuming and is often considered a nuisance by the orthodontist as well as by the patient.

It has been proposed in the past to provide metallic archwire slot liners for plastic brackets, in part as an attempt to avoid deformation of the plastic material. Examples of archwire slot liners are described in U.S. Pat. Nos. 3,964,165, 4,299,569 and 4,302,532. Metallic archwire slot liners for plastic brackets provide sliding mechanics that resemble the sliding mechanics as would be observed when an all-metal bracket is used.

Orthodontic brackets have also been made of translucent ceramic material such as polycrystalline aluminum oxide as is described in U.S. Pat. No. 4,954,080, assigned to the assignee of the present invention. Ceramic is a relatively hard material in comparison to plastic and does not exhibit creep deformation in areas adjacent the archwire slot when subjected to forces of the archwire. However, application of an undue force by the archwire may fracture the bracket, possibly because of localized areas of relatively high stress concentrations.

It has also been observed that the sliding mechanics of a metallic archwire in the slot of a ceramic bracket are not as satisfactory as the sliding mechanics of a metallic wire in the slot of a metal bracket. In one experiment, scanning electron microscope photographs of a stainless steel archwire showed that the archwire had deep scratches after movement along the slot of a ceramic bracket, suggesting that the ceramic material galled the archwire and provided severe mechanical restraint to sliding movement. Unfortunately, undue resistance of a ceramic bracket to sliding movement along an archwire may lengthen treatment time and thus provide an additional expense to both the orthodontist and the patient.

OTHER ART

U.S. Pat. No. 3,504,438 proposes an orthodontic bracket made of a stainless steel or chrome alloy and coated with a polymeric material such as polytetrafluoroethylene to provide a relatively low coefficient of friction for sliding movement of the bracket. U.S. Pat. No. 5,203,804 (which is assigned to the assignee of the present invention) describes the use of a hard carbon coating such as a diamond-like coating on a metallic orthodontic archwire or on a metallic or ceramic orthodontic bracket.

SUMMARY OF THE INVENTION

The present invention in one embodiment relates to an orthodontic bracket that comprises a body having a mesial side, a distal side and an elongated channel extending between the mesial side and the distal side. The bracket includes a liner received in the channel and having an archwire slot. The liner includes an end portion with at least one section that extends over one of the sides in a direction generally parallel to the side.

Another aspect of the invention relates to an orthodontic bracket that comprises a body made of a ceramic material and having an elongated channel. The bracket includes a liner received in the channel and having an archwire slot. The liner is made of a material having a Knoop hardness that is less than the Knoop hardness of the ceramic material.

The invention is also directed toward an orthodontic bracket that comprises a body having an elongated channel with a bottom wall and a liner extending along the channel. The liner has an archwire slot with a bottom surface that is located from the bottom wall a distance that varies along the length of the archwire slot.

Another embodiment of the present invention is related to an orthodontic bracket that comprises a body having an elongated channel and a liner extending along the channel. The liner includes an edgewise archwire slot portion having parallel walls for edgewise therapy. The liner includes mesial and distal archwire slot relief portions that provide occlusal and gingival archwire relief. The mesial and distal archwire slot relief portions are located on mesial and distal sides respectively of the edgewise archwire slot portion.

The invention also concerns an orthodontic bracket comprising a body having a mesial side, a distal side and an elongated channel extending between the mesial side and the distal side. The bracket includes a liner received in the channel and having an archwire slot. The liner includes an end portion having a first section that extends over one of the sides along a direction generally parallel to the side. The end portion includes a second and a third section that extend past the side along a direction generally parallel to the longitudinal axis of the channel.

The invention also is directed toward an orthodontic bracket comprising a body having an elongated channel and a liner received in the channel. The liner has an archwire slot. The bracket includes means for bonding the liner to the body in such a manner that the liner places at least a portion of the body under compression.

The invention also concerns a method of making an orthodontic bracket comprising the steps of providing an orthodontic bracket body having an elongated channel, placing in the channel a liner having an archwire slot, and bonding the liner to the body in such a manner that the liner imparts a compressive force on the body.

DETAILED DESCRIPTION OF THE PREFERRED EMBODIMENTS

Figure 2:
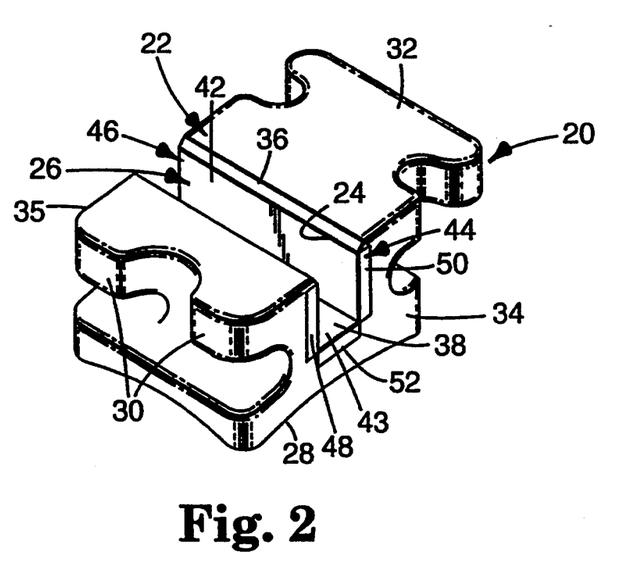
FIG. 2 is a perspective view of a bracket having the liner shown in FIG. 1.

An orthodontic bracket 20 according to one embodiment of the present invention is illustrated in FIG. 2. The bracket 20 includes a ceramic bracket body 22 having an elongated channel 24. A liner 26 is snugly received in the channel 24 in mating fashion and is shown alone in FIG. 3..

The bracket body 22 has a base 28 with a compound contour for attaching the bracket 20 directly to a patient's tooth. A labial face of the body 22 includes a pair of spaced apart occlusal tiewings 30, 30 and a gingival hook 32 having mesial and distal notches. The channel 24 of the body 22 extends from a mesial side 34 to an opposite, distal side 35 along a central, mesial-distal axis of the body 22. A pair of opposed, chamfered wall sections 36 are located between the labial face of the body 22 and the channel 24 to facilitate insertion of an archwire into the liner 26.

Figure 1:
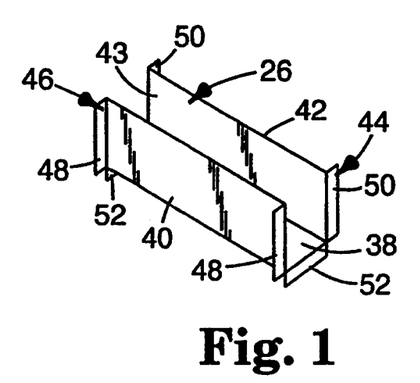
FIG. 1 is a perspective view of a liner for an orthodontic bracket according to one embodiment of the invention.

The liner 26 includes a central portion having a bottom wall 38, an occlusal wall 40 and a gingival wall 42. The occlusal wall 40 and the gingival wall 42 are parallel to each other and extend in a direction perpendicular to the bottom wall 38. The walls 38, 40, 42 present an archwire slot 43 having a U-shaped configuration in a longitudinally transverse reference plane. The U-shaped configuration of the archwire slot 43 matches the cross-sectional shape of a rectangular archwire having similar cross-sectional dimensions, and thus is adapted to complementally receive the archwire in close-fitting relation for orthodontic treatment according to a technique known as edgewise therapy.

The liner 26 includes a mesial end portion 44 and a distal end portion 46 that extend beyond the mesial side 34 and the distal side 35 respectively. Both of the end portions 44, 46 include an occlusal section 48 extending in an occlusal direction, a gingival section 50 extending in a gingival direction, and a lingual section 52 extending in a lingual direction. The sections 48, 50, 52 extend in directions parallel to (and flatly contact) the respective underlying sides 34, 35. In the bracket 20 depicted in FIGS. 1–2, the mesial and distal sides 34, 35 are perpendicular to the longitudinal axis of the archwire slot 43; hence the folded-over sections 48, 50, 52 of the liner end portions 44, 46 extend in respective, common reference planes that are substantially perpendicular to the longitudinal axis of the archwire slot 43. However, it is also possible to construct a bracket according to the invention with mesial and distal sides that extend at an angle other than ninety degrees relative to the longitudinal axis of the archwire slot, in which case the folded-over end portions of the liner would also extend at substantially the same, non-ninety degree angle.

The liner 26 is made of a 0.002 in. (0.05 mm) thick sheet of no. 301 stainless steel, although a gold, titanium or palladium foil sheet may also be utilized. Optionally, the liner 26 is coated with a low friction coating such as the diamond-like coatings that are described in U.S. Pat. No. 5,203,804, the disclosure of which is hereby expressly incorporated into the present disclosure.

The liner 26 is secured in place in the channel 24 by friction, mechanical retention and/or adhesion. The liner 26 may be secured by adhesion to the bracket body 22 by a brazing process, a reaction bonding process or by the use of organic adhesives. Suitable brazing filler materials include molybdenum-manganese paste, platinum, silver or an active metal such as titanium or zirconium.

Reaction bonding may be carried out using a liner 26 made of nickel. Suitable organic adhesives include acrylates, epoxies, hot melt adhesives, pressure sensitive adhesives and urethanes. A satisfactory adhesive is "TRANSBOND" photocurable orthodontic adhesive (from 3M Unitek). Advantageously, the sections 48, 50, 52 engage the mesial side 34 and the distal side 35, facilitating retention of the liner 26 in the channel 24. The adhesive may be omitted provided the liner 26 engages the sides 34, 35 with sufficient force to retain the liner 26 in place by friction.

The bracket body 22 is made of polycrystalline alumina and has sufficient light transmittance to enable the color of the tooth to be reflected through the body 22, so that the body 22 takes on the color of the underlying tooth. Suitable ceramic materials for the body 22 are described in U.S. Pat. No. 4,954,080, the disclosure of which is incorporated by reference herein. In use, most of the liner 26 is positioned behind the archwire and consequently does not significantly lessen the aesthetic nature of the bracket body 22.

The polycrystalline alumina material of the body 22 is relatively hard and brittle, and typically has a Knoop hardness that is greater than 1200 kg/mm$^2$. Advantageously, the material of the liner 26 is relatively soft compared to the material of the bracket body 22, and has a Knoop hardness less than the Knoop hardness of the body 22. More specifically, the liner 26 has a Knoop hardness in the range of 50-1000 kg/mm$^2$, and more preferably in the range of 100-500 kg/mm$^2$. The Knoop hardness of the liner 26 is similar to the Knoop hardness of the archwire in order to reduce the likelihood of galling or abrasive wear of the archwire. The liner 26 also serves to dissipate localized areas of relatively high stress concentrations that might otherwise be imposed by the archwire on the body 22, thereby reducing the likelihood that the body 22 will fracture in use.

In one example, an active metal brazing material (Lucanex 721, Lucas-Milhaupt, Inc.) was dispensed into a channel of a polycrystalline alumina bracket body, and a metallic archwire slot liner having a thickness of 0.002 in. (0.05 mm) was inserted into the channel. Excess brazing material was wiped away and a rectangular mandrel having cross-sectional dimensions equivalent to the desired dimensions of the archwire slot was inserted into the liner to assist in maintaining the archwire slot configuration. The assembly of the bracket body, liner and mandrel was then placed in a furnace and heated to 850° C. in an argon atmosphere for 12 minutes to braze the liner to the ceramic body before cooling. In another example, a similar bracket body, liner and brazing material were placed in a furnace at 850° C. under vacuum for 5 minutes.

Preferably, the liner 26 places the bracket body 22 under compressive forces once the liner 26 is secured to the body 22. In this manner, the relatively brittle ceramic body 22 is pre-stressed by the liner 26 and the bracket 20 exhibits superior torque strength in use (i.e., superior resistance to fracture as an archwire is twisted about its long axis) than what might otherwise be observed. Pre-stressing of the bracket body 22 could be carried out using a mechanism to place the liner 26 under tension as the liner 26 is bonded to the bracket body 22. More preferably, however, the bracket body 22 is pre-stressed by heating the bracket body 22 and the liner 26 as the liner 26 is bonded to the bracket body 22. Upon cooling, the greater thermal contraction of the liner 26 relative to the bracket body 22 enables the liner 26 to thereafter retain the attached body 22 under compression. (The difference in thermal contraction is due to the fact that the thermal expansion coefficient of the liner 26 is greater than the thermal expansion coefficient of the bracket body 22.)

Figure 3:
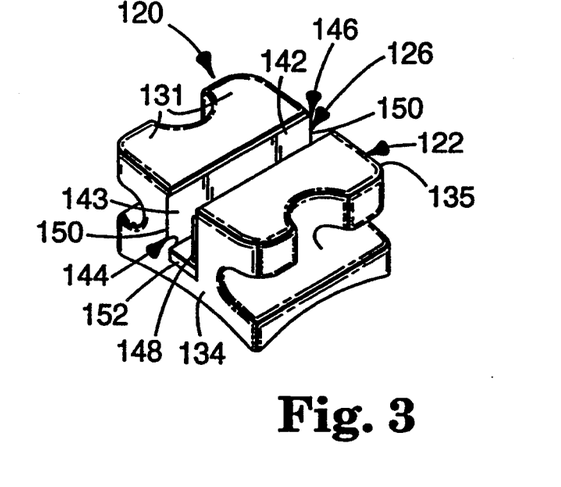
FIG. 3 is a perspective view illustrating a bracket constructed in accordance with another embodiment of the invention.
Figure 4:
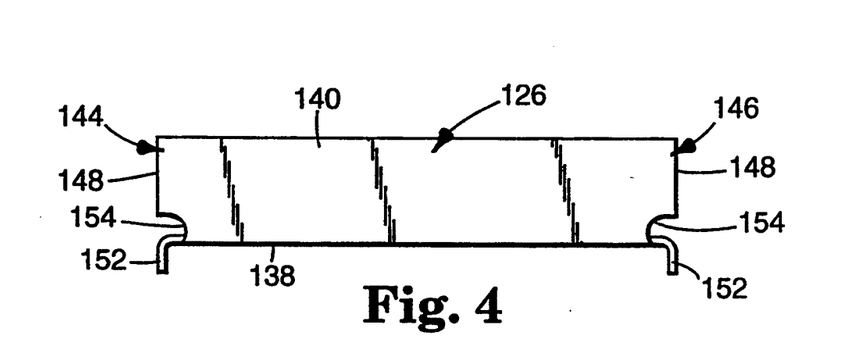
FIG. 4 is an enlarged elevational view of the liner alone that is shown in FIG. 3.

Another embodiment of the invention is shown in FIGS. 3 and 4 and includes a bracket 120 (FIG. 3) having a body 122 somewhat similar to the body 22 shown in FIG. 2, except that the body 122 has a pair of spaced apart gingival tiewings 131 in place of the hook 32. Additionally, a liner 126 of the bracket 120 has end portions 144, 146 that are somewhat different than the end portions 44, 46 described in connection with FIGS. 1 and 2.

More particularly, a lingual section 152 (FIGS. 3-4) of each of the end portions 144, 146 extends flatly over a mesial side 134 and distal side 135 respectively of the bracket body 122 in a direction at a non-zero angle relation to the longitudinal axis of an archwire slot 143. However, the end portions 144, 146 each have an occlusal section 148 and a gingival section 150 that extend parallel to each other in a direction along a mesial-distal reference axis and project slightly (e.g., in the range of about 0.001-0.005 inch) past the respective mesial side 134 and distal side 135 in co-planar relation with an occlusal wall 140 (FIG. 4) and a gingival wall 142 (FIG. 3) respectively of a central portion of the liner 126. The parallel sections 148, 350 reduce the likelihood of the ceramic body 22 coming into contact with an archwire received in the slot 143.

FIG. 4 is an illustration of the liner 126 alone. The liner 126 is made from an initially flat sheet that is provided with notches 154 to facilitate bending the occlusal wall 140 and the gingival wall 142 relative to a bottom wall 138 to form a substantially rectangular, U-shaped configuration in transverse cross-section.

Figures 5, 6:
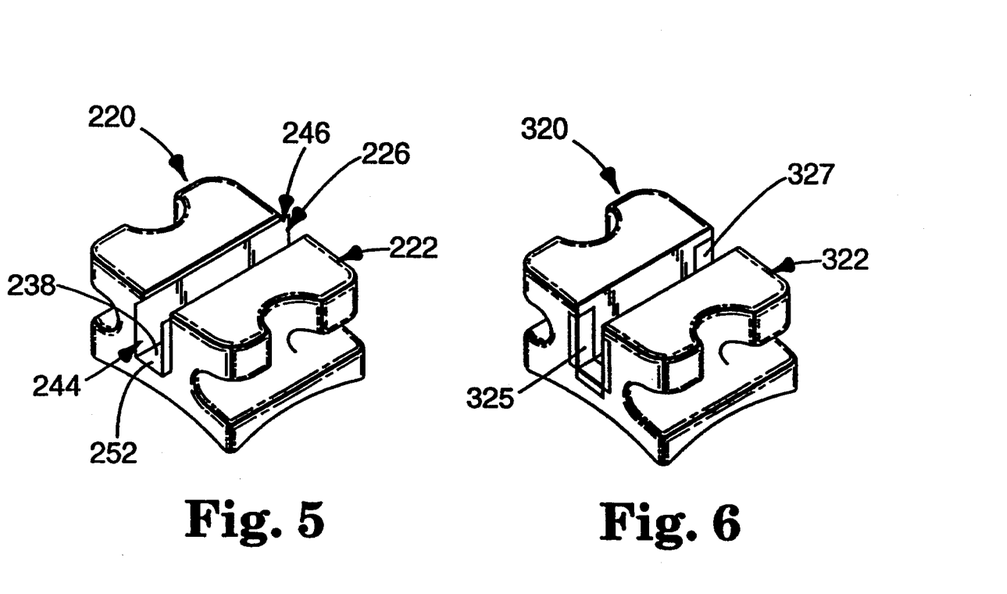
FIG. 5 is a perspective view of a bracket constructed in accordance with another embodiment of the invention.
FIG. 6 is a perspective view of a bracket in accordance with another embodiment of the invention.

The embodiment of the invention that is shown in FIG. 5 concerns a bracket 220 having a body 222 similar to the body 122, and a liner 226 received in a channel of the body 222. The liner 226 is essentially identical to the liner 126, except that lingual sections 252 of outwardly extending end portions 244, 246 are coplanar with a bottom wall 238 of the liner 226.

The bracket 320 that is depicted in FIG. 6 includes a body 322 that is similar to the bodies 122, 222. However, the bracket 320 includes a liner assembly comprised of a mesial liner 325 and a distal liner 327. The liner assembly is essentially identical to the liner 26 depicted in FIGS. 1 and 2, except that a section of the central portion of the liner 26 has been removed, with the result that the mesial liner 325 is spaced apart from the distal liner 327.

Figure 7:
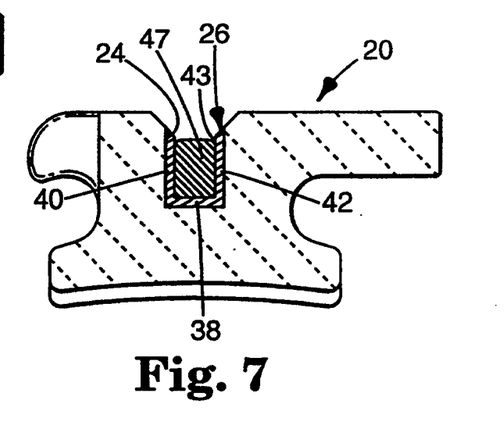
FIG. 7 is an enlarged side view of an orthodontic bracket of the invention that includes a bracket body having a channel and a liner in the channel with an archwire slot having certain cross-sectional dimensions.

FIG. 7 is an enlarged, side cross-sectional view of the bracket 20 shown in FIG. 2. The bottom wall 38, occlusal wall 40 and the gingival wall 42 of the liner 26 are sized to snugly fit within the confines of the channel 24, and also sized to insure that the archwire slot 43 complementally receives a rectangular archwire 47 having cross-sectional dimensions of 0.018×0.025 inch.

Figure 8:
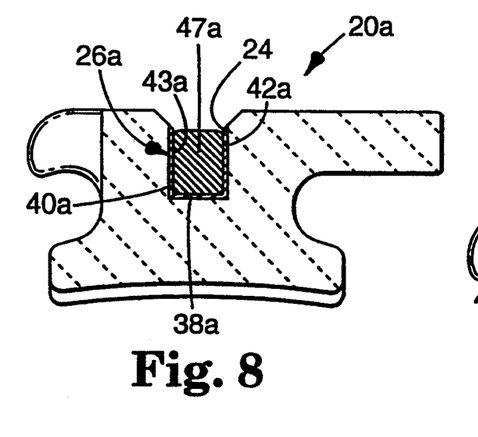
FIG. 8 is an enlarged side view of a bracket body having a channel with dimensions identical to the channel of the bracket body that is shown in FIG. 7, but with a liner received in the channel having somewhat different cross-sectional dimensions to receive an archwire of a different size.

FIG. 8 is a view somewhat similar to FIG. 7, in that the dimensions of a channel 24 of a bracket 20a shown in FIG. 8 are identical to the dimensions of the channel 24 shown in FIG. 7. Moreover, outer surfaces of a liner 26a having a bottom wall 38a, an occlusal wall 40a and a gingival wall 42a are sized to snugly fit within the confines of the channel 24. However, the walls 38a, 40a and 42a of the liner 26a are of a somewhat different thickness than the walls 38, 40, 42 of the liner 26 shown in FIG. 7, and are of sufficient thickness such that an archwire slot 43a is larger in transverse cross-sectional area in comparison to the transverse cross-sectional area of the archwire slot 43 shown in FIG. 7. The archwire slot 43a is sized to complementally receive a rectangular archwire 47a having cross-sectional dimensions of 0.022×0.028 inch.

Advantageously, and as can be understood by reference to FIGS. 7 and 8, the use of liners 26, 26a having walls of differing thicknesses enable the brackets 20, 20a to be made using identical bracket bodies. The liners 26, 26a enable the bodies to snugly receive either of the two sizes of rectangular archwires that are currently in common use, without the necessity of changing the dimensions of the channel 24. In this manner, the channel 24 of both brackets 20, 20a may be cut by a diamond wheel machining process, or molded by an injection molding process, and need not be changed for either of the illustrated brackets 20, 20a. Instead, the dimensions of the liner 26, 26a are selected to compensate for the differing dimensions of the archwires. Such construction may be useful for the manufacturer in reducing the different number of ceramic bracket bodies necessary for inventory, or alternatively may be useful for the orthodontist that desires to replace one liner with another as treatment proceeds to accommodate a differently sized archwire without removing the bracket body 22 from the tooth.

Figure 9:
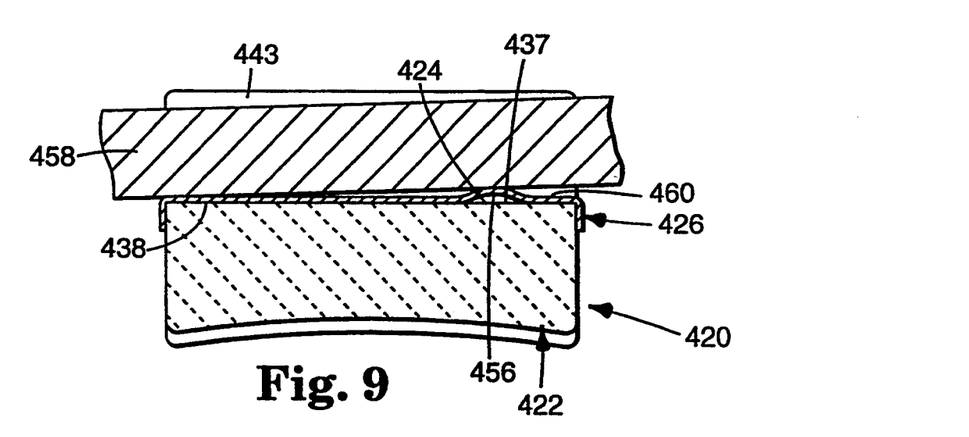
FIG. 9 is a fragmentary, enlarged sectional view of an orthodontic bracket made in accordance with another embodiment of the invention, along with an archwire received in an archwire slot of the bracket.

Referring now to FIG. 9, a bracket 420 includes a body 422 essentially similar to the body 122, and a liner 426 that is received in a channel 424 of the body 422. The liner 426 is substantially similar to the liner 126 illustrated in FIGS. 3 and 4, except that the liner 426 has a bottom wall 438 provided with a bucco-labially extending protrusion or dimple 456 that is located to one side of a central, occlusal-gingival reference axis of the bracket 420.

The dimple 456 of the liner 426 contacts a rectangular archwire 458 that is received in an archwire slot 443 of the liner 426, and causes the archwire 458 to extend at an angle inclined in the range of 2 to 5 degrees from a bottom wall 437 of the channel 424. The inclination of the archwire 458 enables the latter to assist in rotating the tooth attached to the bracket 420 about the tooth's long axis. Occlusal and gingival sides of the archwire 458 flatly contact occlusal and gingival inner surfaces of the liner 426, to enable the archwire 458 to impart tipping or torquing forces when desired to the bracket 420 and the associated tooth according to the treatment technique known as edgewise therapy.

Figure 10:
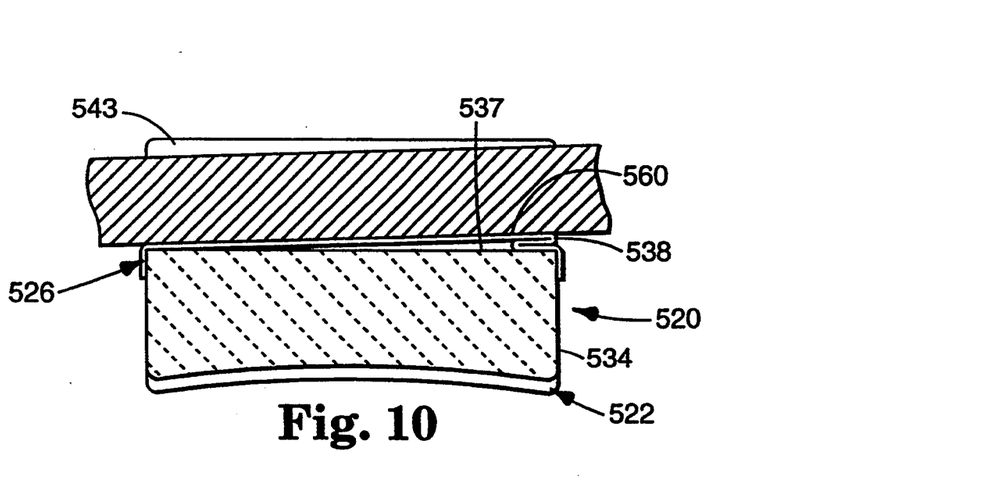
FIG. 10 is a view somewhat similar to FIG. 9 but constructed in accordance with another embodiment of the invention.

The embodiment of the invention that is illustrated in FIG. 10 concerns a bracket 520 having a body 522 essentially identical to the body 422. A liner 526, however, is somewhat different than the liner 426 in that a section of the bottom wall 538 near a mesial side 534 of the bracket body 522 is folded over itself. The folded-over section of the liner 526 as illustrated in FIG. 10 functions essentially similar to the dimple 456 illustrated in FIG. 9, inasmuch as both features provide a means for enabling an inner, bottom bucco-labially facing surface 460, 560 of the bottom walls 438, 538 respectively to be located from the bottom bucco-labially facing channel wall 437, 537 a distance that varies along the length of the archwire slot 443, 543. As shown in FIGS. 9 and 10, the bottom walls 438, 538 include an underside having a portion that is spaced from the bottom wall 347, 537 of the channel.

Figure 11:
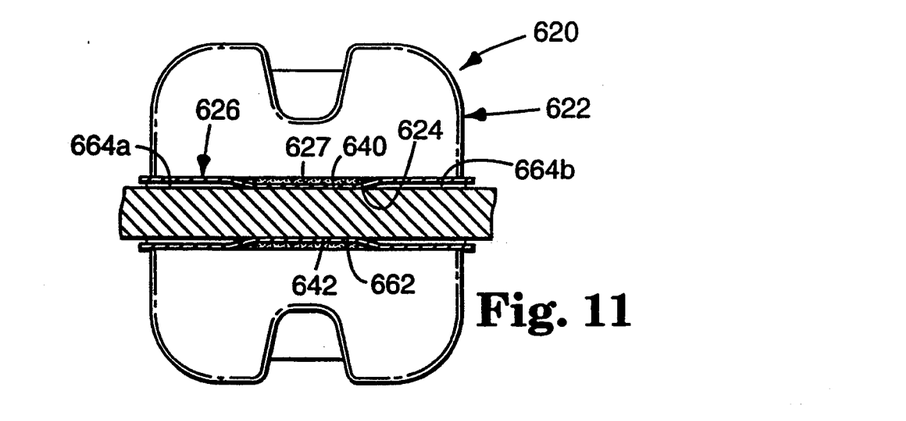
FIG. 11 is a front view of a bracket having a liner that provides mesial and distal archwire slot relief sections and is held in place by double sided adhesive tape in accordance with another embodiment of the invention.

The bracket 620 illustrated in FIG. 11 has a body 622 somewhat similar to the body 122 illustrated in FIG. 3. A channel 624 of the body 622 has a rectangular, U-shaped configuration in transverse cross-section with spaced apart parallel occlusal and gingival walls and a bottom wall that is perpendicular to the occlusal and gingival walls.

A liner 626 of the bracket 620 includes a central edgewise archwire slot section 662 having parallel occlusal and gingival walls 640, 642 for use in the orthodontic treatment procedure known as edgewise therapy. However, the liner 626 also includes mesial and distal archwire slot relief sections 664a, 664b that provide occlusal and gingival archwire relief. The relief sections 664a, 664b are located on mesial and distal sides respectively of the central edgewise archwire slot section 662.

The configuration of the liner 626 illustrated in FIG. 11 advantageously increases the interbracket distance and provides other advantages such as described in U.S. Pat. No. 4,531,911. However, inasmuch as the channel 624 has essentially straight and parallel walls, the channel 624 of the bracket body 622 may be readily machined or molded, while the more complex configuration of the edgewise section 662 and the archwire relief sections 664 is provided in the metal liner 626 that is made, for example, by a metal injection molding process or by a metal forming operation.

The liner 626 is held in place by means of double-sided pressure sensitive adhesive tape 627. Advantageously, the tape 627 is received in the space provided between the edgewise archwire slot section 662 and the bracket body 622, so that additional material of the bracket body 622 need not be removed to accommodate the thickness of the tape 627. Alternatively, however, the tape 627 may extend from the mesial side to the distal side of the bracket body 622. As another alternative, the liner 626 and the tape 627 extend only along the length of the parallel walls 640, 642 and do not substantially extend into the mesial and distal archwire slot relief sections 664a, 664b.

Figure 12:
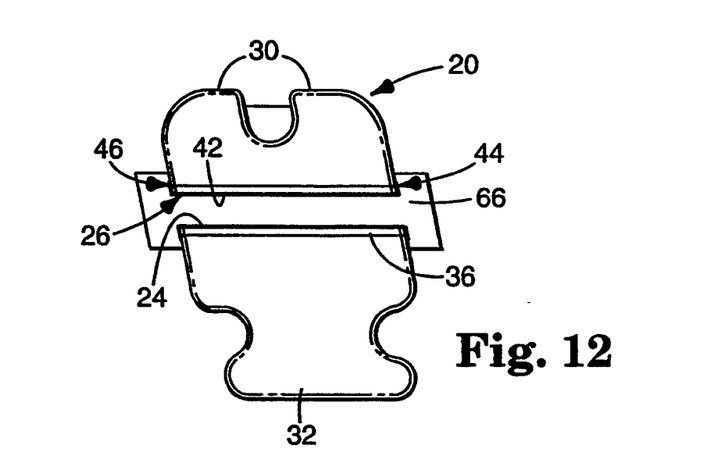
FIG. 12 is a reduced front elevational view of the bracket depicted in FIG. 2 along with a graphite fixture core that is placed in an archwire slot of the bracket liner during a brazing operation in order to affix the liner to the bracket body.

FIG. 12 is a front elevational view of the bracket 20 illustrated in FIG. 2, along with a graphite fixture core 66 that is received in the archwire slot 43. The graphite fixture core 66 retains the liner 26 firmly in place in the channel 24 as the bracket 20 is placed, for example, in an oven in order to braze the liner 26 to the body 22.

Figure 13:
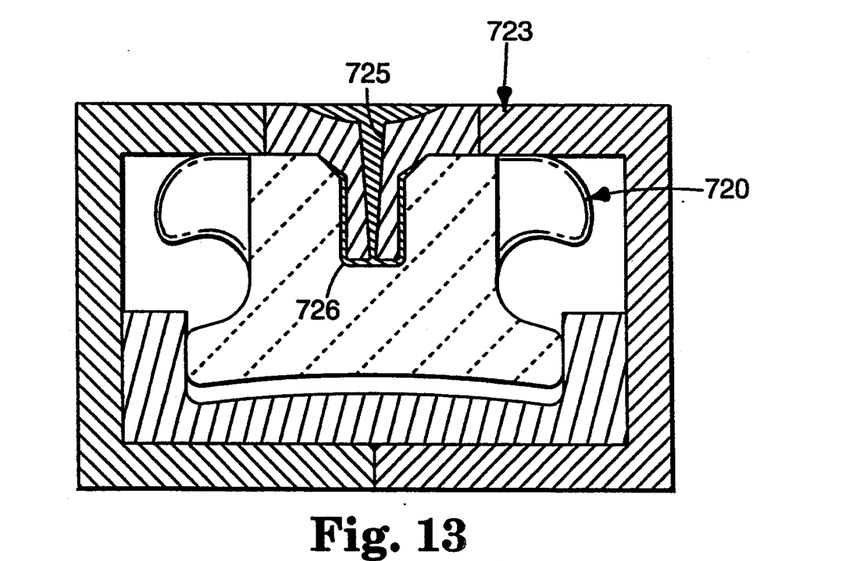
FIG. 13 is an enlarged side cross-sectional view of a bracket according to another embodiment of the invention, showing a bracket body received in a mold assembly during a metal injection molding process for making the liner.

FIG. 13 is an illustration of a bracket 720 having a liner 726 made in situ by a metal injection molding process. The ceramic bracket 720 is placed within a mold assembly 723, and molten metal powder is injected under pressure through a channel 725 in the mold assembly 723 to form the liner 726.

Other in situ processes for forming a liner include the use of colloidal metal paints (such as Pelco Colloidal Silver from Ted Pella, Inc., Redding, Calif.), colloidal metal paints containing glass for improved adhesion (such as Heraeus silver metallization paste No. C1214B, Heraeus, Inc.), active metal brazing materials (such as titanium, zirconium or Lucanex 721, Lucas-Milhaupt, Inc.), molybdenum-manganese brazing materials, electroless plating processes (using plating materials such as nickel, and optionally followed by conventional electroplating using nickel, copper, gold, or other materials), or vapor phase deposition (such as thermal evaporation, sputtering, ion beam deposition, or chemical vapor deposition). Preferably, the selected in situ process prestresses the ceramic bracket body in the manner mentioned above.

Paints or pastes may be applied to the bracket body by dipping an archwire in the paint or paste, and then moving the archwire along the channel of the bracket body. The archwire slot of the liner may be machined after the liner is formed to ensure that the finished archwire slot has the proper cross-sectional dimensions, although preferably the archwire slot has the desired dimensions upon completion of the in situ process so that the need for subsequent machining is avoided.

We claim:

1. An orthodontic bracket comprising a body having a mesial side, a distal side and an elongated channel extending between said mesial side and said distal side, said bracket including a liner received in said channel, said liner having an archwire slot, said liner including an end portion with at least one section that extends over one of said sides along a direction generally parallel to said one side.

2. The bracket of claim 1, wherein said at least one section extends in a lingual direction.

3. The bracket of claim 1, wherein said at least one section extends in an occlusal direction.

4. The bracket of claim 1, wherein said at least one section extends in a gingival direction.

5. The bracket of claim 1, wherein said end portion includes a second section, said second section extending beyond said bracket body in a direction generally parallel to the longitudinal axis of said channel.

6. The bracket of claim 1, wherein said archwire slot has a bottom surface and said channel has a bottom wall, and wherein said surface is located from said bottom wall a distance that varies along the length of said archwire slot.

7. The bracket of claim 1, wherein said mesial side and said distal side are located on mesial and distal extremities respectively of said bracket.

8. An orthodontic bracket comprising a body having an elongated channel with a bottom bucco-labially facing wall and a liner extending along said channel, said liner having an archwire slot with a bottom bucco-labially facing surface, wherein said bottom of said archwire slot liner includes an underside having a portion that is spaced from said bottom of said channel such that said surface is located from said bottom wall a distance that varies along the length of said archwire slot.

9. An orthodontic bracket comprising a body having an elongated channel with a bottom bucco-labially facing wall and a liner extending along said channel, said liner having an archwire slot with a bottom bucco-labially facing surface, said surface being located from said bottom wall a distance that varies along the length of said archwire slot, wherein said liner includes a bottom wall having a dimple.

10. An orthodontic bracket comprising a body having an elongated channel with a bottom bucco-labially facing wall and a liner extending along said channel, said liner having an archwire slot with a bottom bucco-labially facing surface, said surface being located from said bottom wall a distance that varies along the length of said archwire slot, wherein said liner includes a bottom wall having a folded over section.

11. An orthodontic bracket comprising a body having an elongated channel with a bottom bucco-labially facing wall and a liner extending along said channel, said liner having an archwire slot with a bottom bucco-labially facing surface, said surface being located from said bottom wall a distance that varies along the length of said archwire slot, wherein said liner includes an end portion that extends beyond the body in a direction along a mesial-distal reference axis.

12. The bracket of claim 11, wherein said end portion includes at least one section that extends in a direction generally perpendicular to the longitudinal axis of said channel.

13. An orthodontic bracket comprising a body having an elongated channel and a liner extending along said channel, said liner including an edgewise archwire slot portion having parallel walls for edgewise therapy, said liner including mesial and distal archwire slot relief portions providing occlusal and gingival archwire relief and located on mesial and distal sides respectively of said edgewise archwire slot portion.

14. The bracket of claim 13, wherein said liner is made from a sheet of metal.

15. The bracket of claim 13, wherein said liner is made of a metal injection molded material.

16. The bracket of claim 13, including an adhesive located between said edgewise archwire slot portion of said liner and said channel of said bracket.

17. The bracket of claim 16, wherein said adhesive comprises a double-sided pressure sensitive adhesive tape.

18. An orthodontic bracket comprising a body having a mesial side, a distal side and an elongated channel extending between said mesial side and said distal side, said bracket including a liner received in said channel, said liner having an archwire slot, said liner including an end portion having a first section that extends over one of said sides along a direction generally parallel to said one of said sides, said end portion including second and third sections that extend past one side along a direction generally parallel to the longitudinal axis of said channel.

19. An orthodontic bracket comprising a body having an elongated channel and a liner received in said channel, said liner having an archwire slot, and means for bonding said liner to said body in such a manner that said liner is in tension and places said body under compression.

20. The bracket of claim 19, wherein said means comprises a reaction bond.

21. The bracket of claim 19, wherein said means comprises a bond carried out using heat.

22. A method of making an orthodontic bracket comprising the steps of providing an orthodontic bracket body having an elongated channel, placing in the channel a liner having an archwire slot, and bonding the liner to the body in such a fashion that the liner is in tension and places the body under compression.

23. The method of claim 22, wherein said step of bonding the liner to the body is carried out at temperatures above atmospheric.

* * * * *

UNITED STATES PATENT AND TRADEMARK OFFICE
CERTIFICATE OF CORRECTION

PATENT NO. : 5,380,196

DATED : January 10, 1995

INVENTOR(S) : John S. Kelly, James D. Hansen and Joseph M. Caruso

It is certified that error appears in the above-indentified patent and that said Letters Patent is hereby corrected as shown below:

Col. 6, line 17, "350" should read -- 150 --.

Col. 7, line 52, "wail" should read -- wall --.

Col. 7, line 56, "347" should read -- 437 --.

Col. 10, line 33, insert -- said -- after "past".

Signed and Sealed this

Twenty-ninth Day of August, 1995

Attest:

BRUCE LEHMAN

*Attesting Officer*    *Commissioner of Patents and Trademarks*